US00PP08370P

United States Patent [19]

van der Knaap

[11] Patent Number: Plant 8,370

[45] Date of Patent: Sep. 14, 1993

[54] CHRYSANTHEMUM PLANT—WHISPER CULTIVAR

[75] Inventor: Jacques C. M. van der Knaap, De Lier, Netherlands

[73] Assignee: Fides Beheer B.V., De Lier, Netherlands

[21] Appl. No.: 902,900

[22] Filed: Jun. 23, 1992

[51] Int. Cl.[5] ..... A01H 5/00

[52] U.S. Cl. ..... Plt./82.4

[58] Field of Search ..... Plt./74.1, 82.4, 82.5, Plt./80, 76

*Primary Examiner*—Howard J. Locker

*Attorney, Agent, or Firm*—Burns, Doane, Swecker & Mathis

[57] ABSTRACT

A new and distinct cultivar of Chrysanthemum plant named Whisper is provided. The new cultivar was the result of a controlled breeding program wherein an unnamed plant designated 84.824 was pollinated by an unnamed plant designated 84.762. More specifically, the new cultivar forms attractive relatively small bicolored flowers wherein the petals are pink and the disc florets a yellow changing to white with full maturity. The inflorescence tends to be flat in configuration when mature. The plant is vigorous and forms attractive dark green foliage. The response period of the flowers in approximately eight and one-half weeks. Resistance to white rust is exhibited. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Whisper.

The new cultivar is the product of a planned breeding program which had as its objective the creation of a new Chrysanthemum cultivar which exhibits attractive relatively small pink anemone bicolored flowers, a desirable response period, resistance to white rust, and the ability to produce flowers of commercially acceptable quality throughout the year in a cut mum production program. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1985 at De Lier, The Netherlands. The female parent (i.e., the seed parent) was an unnamed plant designated 84.824 and the male parent (i.e., the pollen parent) was an unnamed plant designated 84.762. The parentage of the new cultivar can be summarized as follows:

84.824 × 84.762.

The seeds resulting from the above pollination were sown and plantlets were obtained which were physically and biologically different from each other. Selective study during November, 1985 resulted in the identification of a single plant of the new variety.

It was found that the new cultivar of the present invention:

(a) exhibits attractive relatively small anemone flowers having an overall diameter of approximately 40 mm. wherein the petals are pink and the disc florets form a cushion which changes from yellow to white as the flowers mature, (b) bears flowers having a somewhat flat capitulum, (c) exhibits a flower response period of approximately eight and one-half weeks, (d) exhibits considerable vigor and forms attractive dark green foliage, (e) has the ability to produce flowers of commercially acceptable quality throughout the year in a cut mum production program, and (f) exhibits resistance to white rust.

Asexual reproduction of the new cultivar by cuttings initially taken during January, 1986, as preformed at De Lier, The Netherlands, in a controlled environment has demonstrated that the characteristics of the new cultivar as herein disclosed are firmly fixed and are retained through successive generations of asexual propagation.

Whisper has not been observed under all possible environmental conditions at date. Accordingly, it is possible that the phenotype may vary somewhat with variations in the environment, such as temperature, light, day length, contact with pesticides and/or subjection to growth retardant treatments.

When the new cultivar of the present invention is compared to the Sarina cultivar (non-patented in the United States), the Whisper cultivar is found to form smaller flowers (as illustrated), to exhibit more vigor, and to exhibit a slower response period (e.g., 8½ weeks vs. 8 weeks).

BRIEF DESCRIPTION OF THE PHOTOGRAPH

The accompanying photograph shows as nearly true as it is resonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined on Jul. 8, 1991 at 11:00 a.m. to 12:00 noon under natural daylight conditions at De Lier, The Netherlands. The plants described were grown under standard greenhouse conditions which approximate those commonly utilized for the production of cut mums.

Classification:

*Botanical.*—*Chrysanthemum morifolium* Ramat., cv. Whisper.

*Commercial.*—Cut anemone spray.

Inflorescence

A. Capitulum:

*Form.*—Flat.

*Type.*—Anemone.

*Diameter across face.*—Approximately 40 mm. on average.

B. Corolla of ray and disc florets:

*Color* (*General tonality from a distance of three meters*).—Pink with dissimilar center coloration.

*Color ray florets.*—Top surface.—Pink, red-purple group 73D. Under surface.—Pink, red-purple group 73D.

*Color disc florets.*—Immature.—Light green, yellow-green group 150A. Mature.—Yellow, yellow group 6A, changing to white upon full maturity.

C. Reproductive organs:

*Androecium.*—Present in disc florets.

*Gynoecium.*—Present in both ray and disc florets.

Plant

A. General appearance:

*Height.*—Commonly in excess of 100 cm. (e.g., 110 cm.).

B. Foliage:

*Color* (*upper surface*).—Yellow-green group 147A.

*Color* (*under surface*).—Yellow-green group 147B.

I claim:

1. A new and distinct cultivar of Chrysanthemum plant named Whisper, substantially as herein shown and described, which:

(a) exhibits attractive relatively small anemone flowers having an overall diameter of approximately 40 mm. wherein the petals are pink and the disc florets form a cushion which changes from yellow to white as the flowers mature, (b) bears flowers having a somewhat flat capitulum, (c) exhibis a flower response period of approximately eight and one-half weeks, (d) exhibits considerable vigor and forms attractive dark green foliage, (e) has the ability to produce flowers of commercially acceptable quality throughout the year in a cut mum production program, and (f) exhibits resistance to white rust.

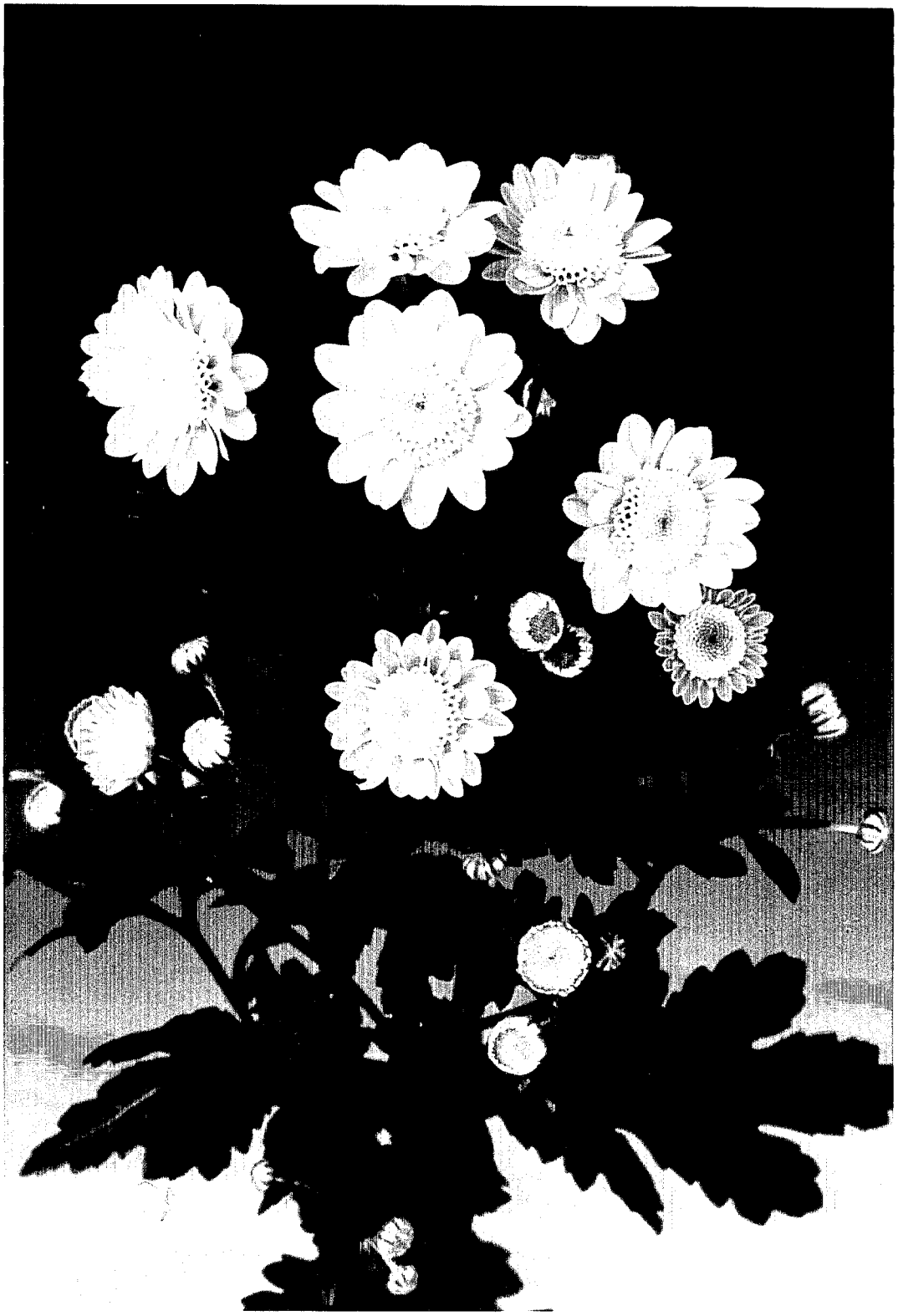

* * * * *